US007839971B2

(12) United States Patent
Bendahan et al.

(10) Patent No.: US 7,839,971 B2
(45) Date of Patent: Nov. 23, 2010

(54) SYSTEM AND METHOD FOR INSPECTING CONTAINERS FOR TARGET MATERIAL

(75) Inventors: Joseph Bendahan, San Jose, CA (US); Walter Irving Garms, Berkeley, CA (US); Mengqian Gu, Newark, CA (US)

(73) Assignee: Morpho Detection, Inc., Newark, CA (US)

( * ) Notice: Subject to any disclaimer, the term of this patent is extended or adjusted under 35 U.S.C. 154(b) by 61 days.

(21) Appl. No.: 12/006,119

(22) Filed: Dec. 31, 2007

(65) Prior Publication Data

US 2009/0168949 A1 Jul. 2, 2009

(51) Int. Cl.
*G01N 23/04* (2006.01)
(52) U.S. Cl. .................................. 378/57; 378/4; 378/5
(58) Field of Classification Search .................... 378/57
See application file for complete search history.

(56) References Cited

U.S. PATENT DOCUMENTS

| 4,029,963 A | 6/1977 | Alvarez et al. |
| 5,182,764 A | 1/1993 | Peschmann |
| 5,367,552 A | 11/1994 | Peschmann |
| 7,116,751 B2 | 10/2006 | Ellenbogen et al. |
| 7,224,763 B2 | 5/2007 | Naidu et al. |
| 2003/0147489 A1 | 8/2003 | Bijjani |
| 2005/0031076 A1 * | 2/2005 | McClelland et al. .......... 378/57 |
| 2007/0121783 A1 | 5/2007 | Ellenbogen et al. |

OTHER PUBLICATIONS

European Patent Office, Patent Cooperation Treaty, Invitation to Pay Additional Fees and including Communication Relating to the Results of the Partial International Search Report for Application No. PCT/US2008/086237, Sep. 25, 2009, 10 pages.

* cited by examiner

*Primary Examiner*—Edward J Glick
*Assistant Examiner*—Mona M Sanei
(74) *Attorney, Agent, or Firm*—Armstrong Teasdale LLP (57) ABSTRACT

A method for automatically inspecting a container for a target material using a computed tomography (CT) scanning system includes performing an initial radiographic scan of the container. Based at least partially on projection data generated during the initial radiographic scan, at least one location within the container is identified that requires CT inspection. A dual energy CT scan of the at least one identified location within the container is performed based on a single energy algorithm or a dual energy algorithm. The dual energy CT scan includes a low energy scan of the at least one identified location and a high energy scan of the at least one identified location. Based on dual energy scan information generated during the dual energy CT scan, a determination is made to confirm or clear an alarm corresponding to the at least one identified location within the container.

28 Claims, 5 Drawing Sheets

SYSTEM AND METHOD FOR INSPECTING CONTAINERS FOR TARGET MATERIAL

FIELD OF THE INVENTION

The field of the invention relates generally to a system and a method for automatically inspecting containers for concealed objects and, more particularly, to a system and a method to efficiently and reliably scan concealed objects for target materials using X-ray computed tomography.

BACKGROUND OF THE INVENTION

Since the events of Sep. 11, 2001, the Department of Homeland Security has increased security dramatically in U.S. airports. Such security efforts include screening passengers and carry-on bags and luggage for concealed contraband, such as explosive materials, drugs and/or weapons.

At least some known security scanning systems employ X-ray transmission technology. Although these systems enable the detection of weapons and blades, for example, they lack the capability of efficiently detecting small quantities of explosive materials with a low false alarm rate. Computed tomography (CT) provides a quantitative measure of material characteristics, regardless of location or the superposition of objects, and a substantial advantage over conventional and multi-view X-ray transmission and radioisotope-based imaging systems. In a CT scanner, a large number of precise X-ray "views" are obtained at multiple angles. These views are then used to reconstruct planar or volumetric images. The image is a mapping of the X-ray mass attenuation value for each volume element (or voxel) within the imaged volume.

Systems employing, for example, CT scanners are used widely in airports around the world on checked luggage to detect explosives that pose a threat to aviation safety. These systems employ an X-ray source and opposing detectors that detect X-ray radiation that passes through an object, e.g., a suitcase, as the object is translated along a conveyor.

At least some known scanning systems are capable of detecting most explosive materials and/or other contraband. However, false alarms are occasionally raised due to similarities shared by explosive materials, other contraband and benign materials. Thus, there is a need to reduce the false alarms.

One method employed for clearing alarms includes determining, in addition to the CT number, the effective atomic number of a suspect object. This may be achieved employing a scanner that provides dual energy information. Standard methods include utilization of energy sensitive detectors, dual energy beams, and filtering. Energy-sensitive detectors facilitate collecting data simultaneously at two or more energies. Some of the energy-sensitive detectors are sophisticated and expensive but may be desirable when the throughput is critical and the additional cost is acceptable. The utilization of filters, either at the source or at the detectors, results in small atomic number separation and might not be sufficient for distinguishing the target material from other materials.

Atomic number information may also be collected by irradiating objects at two or more energies. Utilization of dual energy beams is most efficient when the same volume is inspected with two different energies. This reduces the artifacts due to misregistration. One efficient way is to switch the voltage of the x-ray tube very fast in such a way that the gantry moves a very small angle between energies. This requires a very fast-switching x-ray source, which is not readily available at the required timing, voltages and currents used in some CT systems.

An algorithm employed to determine the effective atomic images in CT scanners requires low and high energy projections (sinograms), which are obtained by any of the methods described above. The algorithm consists of employing system model or calibrated parameters that are tuned to match measured projection values for specific basis-materials. The sinograms are then reconstructed to form basis-material images, which are combined to form effective atomic number images. Alternatively, image-based decomposition is applied after the reconstruction.

At least one CT system utilized for checked luggage explosive detection includes a prescan stage to identify a small number of CT scans. The resulting CT scan data is then used to automatically identify explosives or other objects of interest. These scanners operate in the step-and-shoot mode, wherein the slices are collected with the scanned object in a stationary position.

BRIEF DESCRIPTION OF THE INVENTION

In one aspect, a method for automatically inspecting a container for a target material using a computed tomography (CT) scanning system is provided. The method includes performing an initial radiographic scan of the container. Based at least partially on projection data generated during the initial radiographic scan, at least one location within the container is identified that requires CT inspection. A dual energy CT scan of the at least one identified location within the container is performed based on a single energy algorithm or a dual energy algorithm. The dual energy CT scan includes a low energy scan of the at least one identified location and a high energy scan of the at least one identified location. Based on dual energy scan information generated during the dual energy CT scan, a determination is made to confirm or clear an alarm corresponding to the at least one identified location within the container.

In another aspect, a computed tomography (CT) scanning system for automatically inspecting a container for a target material is provided. The CT scanning system is configured to perform an initial radiographic scan of the container. Based at least partially on projection data generated during the initial radiographic scan, at least one location within the container that may require additional inspection is identified. A slice plan of the at least one identified location is generated and a dual energy CT scan of the at least one identified location is performed based on a single energy algorithm or a dual energy algorithm. The dual energy CT scan includes a low energy scan of the at least one identified location and a high energy scan of the at least one identified location. Based at least partially on dual energy scan information generated during the dual energy CT scan, a determination is made whether to clear the container.

In another aspect, a computed tomography (CT) scanning system for automatically inspecting a container for a target material is provided. The CT scanning system is configured to perform an initial radiographic scan of the container. Based at least partially on projection data generated during the initial radiographic scan, a slice plan with at least one location within the container that may require a single energy CT inspection is identified. The slice plan is adjusted as additional single energy scans are performed. Once the slice plan requires no more single energy scans, an automatic detection algorithm is used to identify objects of interest. If one or more objects of interest are identified, a slice plan of the at least one object of interest is generated and a dual energy CT scan of the at least one identified object of interest is performed. The dual energy CT scan includes a low energy scan of the at least one identified object of interest and a high energy scan of the at least one identified object of interest. Based at least partially on dual energy scan information generated during the dual energy CT scan, a determination is made whether the object contains a target material. If one or more objects contain the target material an alarm signal is generated for the container.

BRIEF DESCRIPTION OF THE DRAWINGS

FIGS. 1-5 show exemplary embodiments of a system and a method described herein.

DETAILED DESCRIPTION OF THE INVENTION

The embodiments described herein provide a system and a method for efficiently and reliably inspecting containers employing dual-energy scanning to verify whether an object within the container is a target material, such as an explosive material, that requires further inspection. If the object is not a target material, the container is cleared. In one embodiment, the system includes a radiographic prescan stage to identify areas or locations of interest within the container. A dual-energy CT scanning performed at these identified locations facilitates identifying one or more objects contained within the container as target materials. Additional processing is performed on each identified object to confirm or clear the target material. In an alternative embodiment, the system includes a radiographic prescan stage to identify areas of interest, a first high-energy CT scanning process to facilitate identifying one or more objects contained within the container, and a second low-energy or dual-energy CT scanning process for determining whether each object includes a target material. The radiographic prescan stage, the first CT scanning process and the second CT scanning process may be performed using a single scanner or may be performed using separate scanners.

Moreover, the embodiments described herein provide technical effects including, without limitation, reducing the occurrence of false alarms by efficiently and reliably performing a targeted secondary scan or additional processing of each identified object to verify whether each identified object includes a target material, thereby separating false alarms from true alarms.

At least one embodiment of the present invention is described below in reference to its application in connection with and operation of a system for inspecting checked luggage for target materials including, without limitation, explosive materials. However, it should be apparent to those skilled in the art and guided by the teachings herein provided that the invention is likewise applicable to any suitable system for scanning containers including, without limitation, cargo containers, boxes, drums, suitcases, and luggage, transported by water, land, and/or air, as well as other containers and/or objects. Further, the system as described herein may be suitable for inspecting checked luggage and/or other containers for target materials other than explosive materials including, without limitation, other contraband such as drugs and/or weapons.

Moreover, although embodiments of the present invention are described below in reference to application in connection with and operation of a system incorporating an X-ray computed tomography (CT) scanning system for inspecting containers, it should be apparent to those skilled in the art and guided by the teachings herein provided that any suitable scanning system including any suitable radiation source including, without limitation, neutrons or gamma rays, may be used in alternative embodiments.

Figure 1:
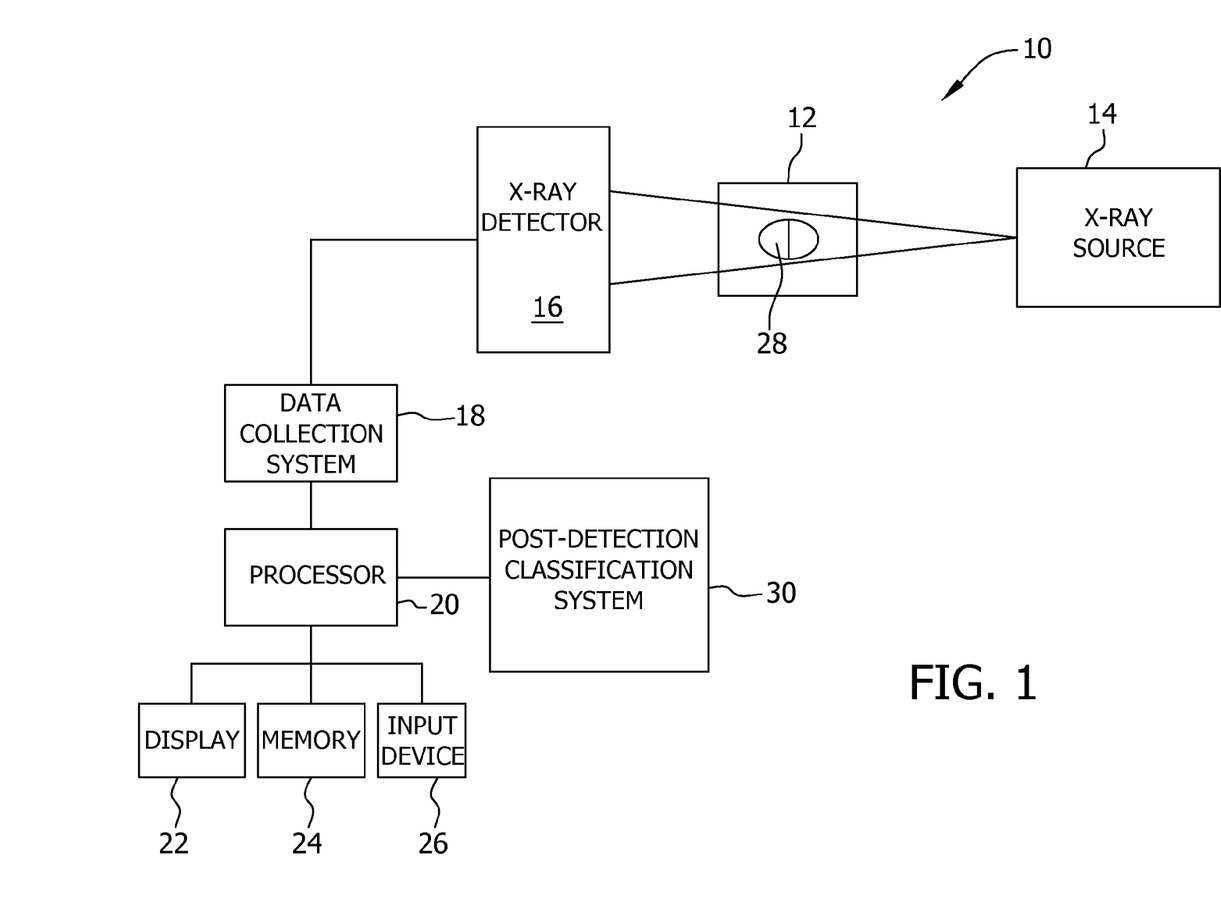
FIG. 1 is a block diagram of an exemplary system for inspecting containers for target materials.

FIG. 1 is a block diagram of an exemplary embodiment of an X-ray computed tomography (CT) scanning system 10 for automatically inspecting a container 12, such as a suitcase, a piece of luggage, a bag, a cargo container, a box, or a parcel, to identify the contents and/or determine the type of material contained within container 12. The term "contents" as used herein generally refers to any object and/or material contained within container 12 and may include contraband. In one embodiment, container 12 is positioned on a conveyor (not shown) and conveyed through scanning system 10.

Scanning system 10 includes at least one X-ray source 14 configured to transmit at least one beam of radiation through container 12. In a particular embodiment, scanning system 10 includes a plurality of X-ray sources 14 configured to emit radiation of different energy distributions. Alternatively, each X-ray source 14 is configured to emit radiation of selective energy distributions, which can be emitted at different times. In a particular embodiment, scanning system 10 utilizes multiple-energy scanning to obtain an attenuation map for container 12. In addition to the production of CT images, multiple-energy scanning enables the production of density maps and atomic number(s) of objects concealed within container 12. In one embodiment, the dual energy CT scanning of container 12 includes inspecting container 12 by scanning container 12 at a low energy distribution and then scanning container 12 at a high energy distribution. The data or scan information is collected for the low energy scan and the high energy scan to reconstruct the CT, density and/or atomic number images of container 12 to facilitate identifying the type of material or contraband within container 12 based on the material content of container 12, as described in greater detail below.

In one embodiment, scanning system 10 also includes at least one X-ray detector 16 configured to detect radiation emitted from X-ray source 14 and transmitted through container 12. X-ray detector 16 is configured to cover an entire field of view or only a portion of the field of view. Upon detection of the transmitted radiation, each X-ray detector element generates a signal representative of the detected transmitted radiation. The signal is transmitted to a data collection system and/or a processor as described below. Scanning system 10 is utilized to reconstruct a CT image of container 12 in real time, non-real time, or delayed time.

Scanning system 10 facilitates obtaining a large number of precise X-ray views or slices, which are then used to reconstruct a volumetric image of container 12. The image is a mapping of the CT number, which approximates the density of container 12, for each volume element regardless of the superposition of objects or materials within container 12. In one embodiment, an imaging system is coupled to X-ray detectors 16 to process the image data for producing a two-dimensional or three-dimensional map of the container and its contents. The reconstructed images are processed to determine a CT number, density and/or atomic number of objects within container 12 being scanned. Analysis of these images facilitates determining the type of material contained within container 12, for example.

In one embodiment of scanning system 10, a data collection system 18 is operatively coupled to and in signal communication with X-ray detector 16. Data collection system 18 is configured to receive the signals generated and transmitted by X-ray detector 16. One or more processors 20 are operatively coupled to data collection system 18. As used herein, the term "processor" is not limited to only integrated circuits referred to in the art as a processor, but broadly refers to a computer, a microcontroller, a microcomputer, a programmable logic controller, an application specific integrated circuit and any other programmable circuit. In one embodiment, scanning system 10 also includes a display device 22, a memory device 24 and/or an input device 26 operatively coupled to data collection system 18 and/or processor 20. The processor may also include a storage device and/or an input device, such as a mouse and/or a keyboard.

During operation of an embodiment of scanning system 10, X-ray source 14 emits X-rays in an energy range, which is dependent on a voltage applied by a power source to X-ray source 14. A primary beam is generated and passes through container 12, and X-ray detector 16, positioned on the opposing side of container 12, measures an intensity of the primary beam.

In one embodiment, a post-detection classification system 30 is operatively coupled, such as in data transmission communication, with scanning system 10, such as operatively coupled to processor 20, and configured to facilitate verification of target materials, as described in greater detail below. Alarms raised by scanning system 10 for suspected contraband are processed by post-detection classification system 30 using a set of image element features and knowledge discovery techniques to facilitate separating false alarms from true alarms. Two-dimensional image pixels and/or three-dimensional image voxels may be used to calculate the image features. Each pixel or voxel represents, for example, a CT value that corresponds to a material.

In one embodiment, dual energy data is processed employing an algorithm to determine the CT number image and/or the effective atomic number image of each identified object. This information is employed with the CT image to determine whether each identified object includes a target material.

Figure 2:
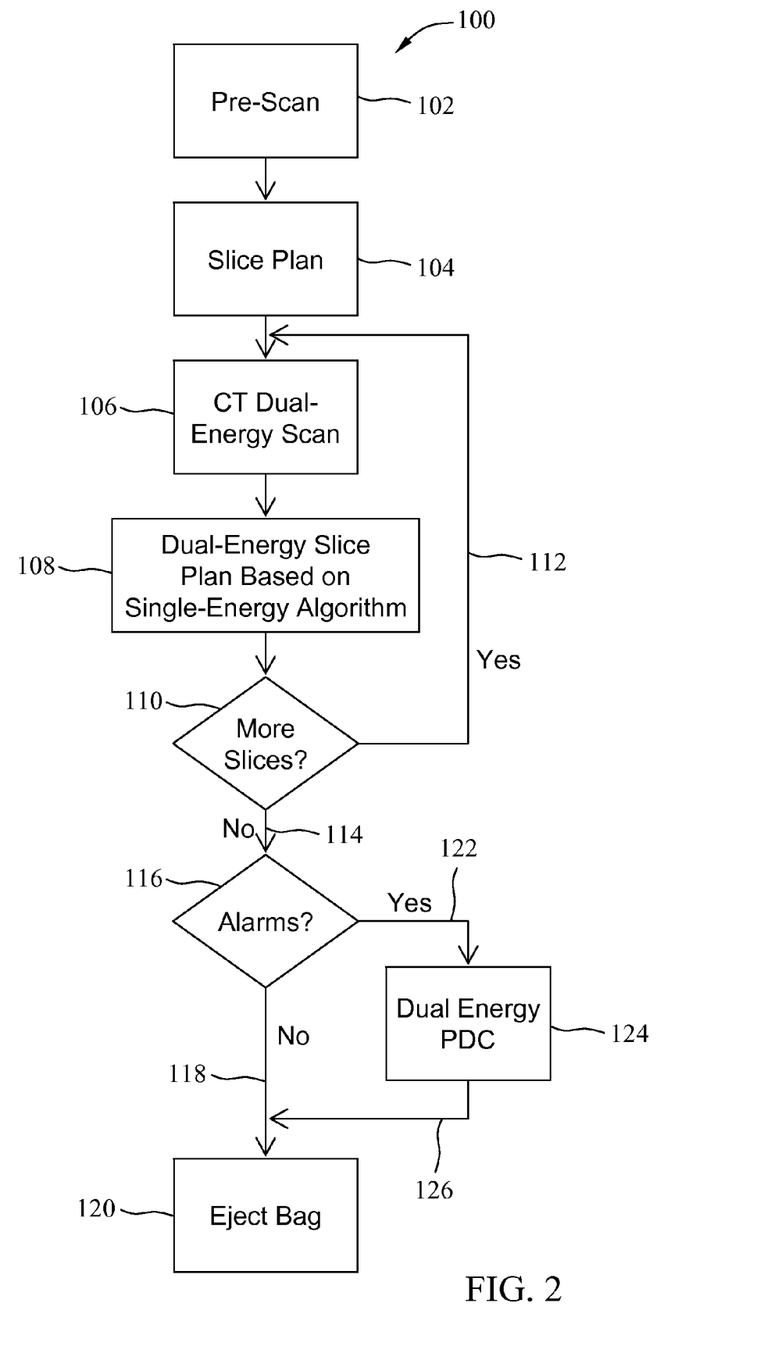
FIG. 2 shows a flow chart for an exemplary method for inspecting containers for target materials using the system shown in FIG. 1.

FIG. 2 shows a flow chart illustrating an exemplary method 100 for inspecting container 12, such as break bulk cargo, to identify one or more objects concealed within container 12 and performing additional processing to verify whether each identified object contains a target material, such as explosive material.

Referring further to FIG. 2, a prescan stage 102 is employed to perform a scan of container 12. In one embodiment, a suitable X-ray radiographic scan of container 12 is performed during prescan stage 102 to identify locations within container 12 that require CT inspection. Based at least partially on projection data generated during prescan stage 102, a first or initial slice plan is generated 104.

In this embodiment, one or more locations within container 12 identified based on a dual energy algorithm are scanned 106 using a dual energy CT scanner. Dual energy CT scan 106 includes a low energy scan and a high energy scan of one or more identified locations within container 12. An updated slice plan is generated 108 based on a single-energy algorithm. Data collection system 18 and/or processor 20 processes the data collected to facilitate the determination 110 whether one or more additional slices are required.

If it is determined that one or more additional slices are required 112 to facilitate determining whether object 28 detected within container 12 includes a target material, the corresponding identified location within container 12 is scanned using the dual energy CT scanner. An updated dual energy slice plan is generated 108 using a single-energy algorithm. Such process is repeated until no additional slice is required 114, and scanning system 10 makes a determination 116 based on available information to clear 118 container 12 or generate an alarm signal indicating that an object within container 12 may include a target material.

However, if there are alarming objects 122, additional processing is performed 124 employing a dual-energy Post-Detection Classifier or other suitable algorithm to clear 126 the object alarm status and eject 120 container 12 or to maintain the object alarm status.

Figure 3:
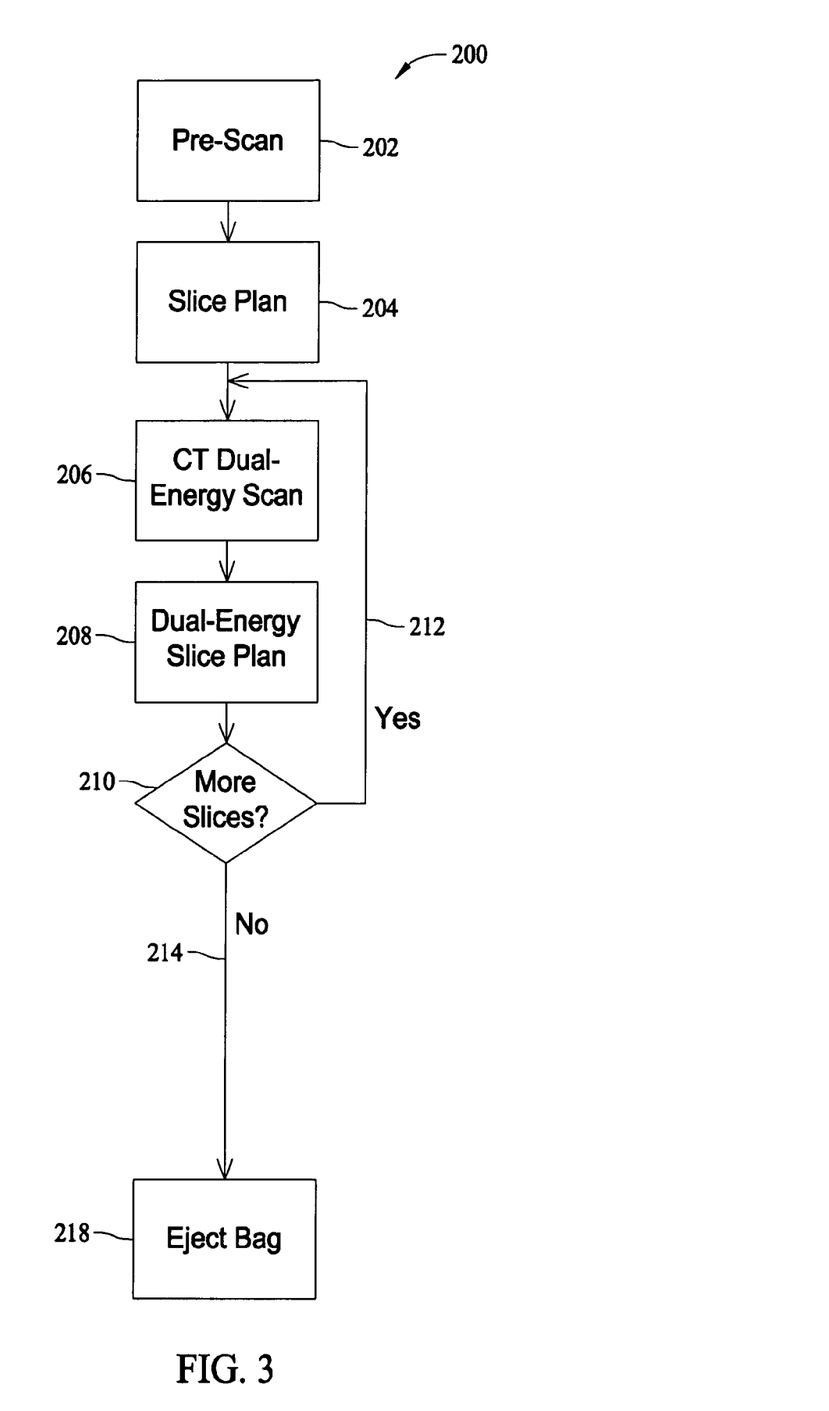
FIG. 3 shows a flow chart for an alternative exemplary method for inspecting containers for target materials using the system shown in FIG. 1.

FIG. 3 shows a flow chart illustrating an alternative exemplary method 200 for inspecting container 12, such as checked luggage, to identify one or more objects concealed within container 12 and performing processing of each identified object to verify whether the object is a prohibited item, e.g., a target material, such as an explosive material.

Referring further to FIG. 3, a prescan stage 202 is employed to perform a scan of container 12. In one embodiment, a suitable X-ray radiographic scan of container 12 is performed during prescan stage 202 to identify locations within container 12 that require CT inspection. As described in greater detail below, based at least partially on projection data generated during prescan stage 202, a first or initial slice plan is generated 204.

In this embodiment, one or more locations within container 12 identified based on a dual energy algorithm are scanned 206 using a dual energy CT scanner. Dual energy CT scan 206 includes a low energy scan and a high energy scan of one or more identified locations within container 12. An updated slice plan is generated 208 based on a dual-energy algorithm. Data collection system 18 and/or processor 20 processes the data collected to facilitate the determination 210 whether one or more additional slices are required.

When no additional slice is required 214, scanning system 10 makes a determination based on available information to clear and eject 218 container 12 from within scanning system 10. However, if it is determined that one or more additional slices are required 212 to facilitate determining whether object 28 detected within container 12 includes a target material, the corresponding identified location within container 12 is dual energy CT scanned 206 using the dual energy CT scanner. An updated dual energy slice plan is generated 208 using the high energy scan information and the low energy information obtained during CT scan 206. Such process is repeated until no additional slice is required 214, and scanning system 10 makes a determination based on available information to clear and eject 218 container 12 from within scanning system 10.

Figure 4:
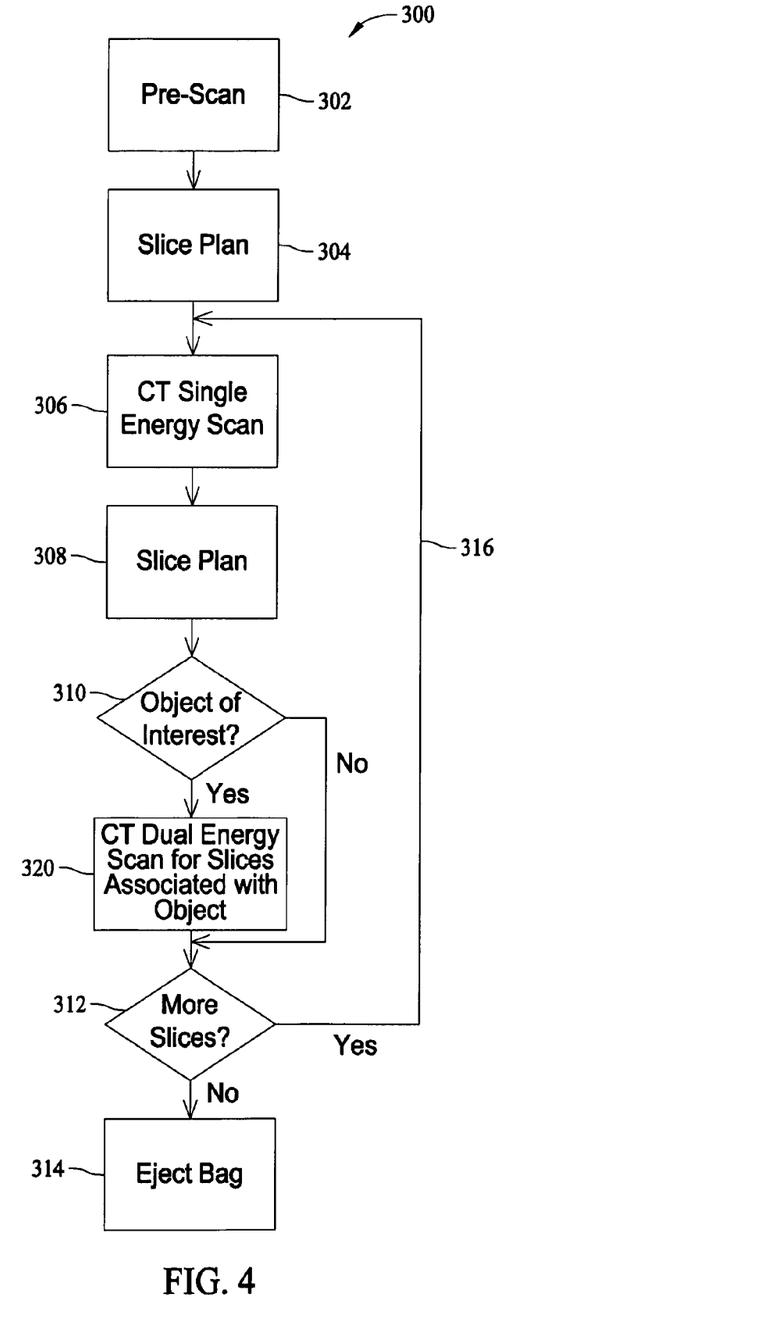
FIG. 4 shows a flow chart for an alternative exemplary method for inspecting containers for target materials using the system shown in FIG. 1.

FIG. 4 shows a flow chart illustrating an alternative exemplary method 300 for inspecting container 12, such as checked luggage, to identify one or more objects concealed within container 12 and performing a targeted scan of each identified object to verify whether the object is a safety threat, e.g., a target material, such as an explosive material.

Referring further to FIG. 4, a prescan stage 302 is employed to perform a scan of container 12. In one embodiment, a suitable X-ray radiographic scan of container 12 is performed during prescan stage 302 to identify locations within container 12 that may require additional inspection. As described in greater detail below, based at least partially on projection data generated during prescan stage 302, a first or initial slice plan is generated 304. Using a suitable algorithm, scanned data corresponding to additional cross-sectional slices of container 12 are obtained and transmitted to data collection system 18 (shown in FIG. 1). In one embodiment, data collection system 18 and/or processor 20 (shown in FIG. 1) processes the data collected to facilitate identifying one or more objects 28 of interest within container 12. In this embodiment, only identified objects 28 are dual energy CT scanned. As a result, suitable system throughput is maintained because only slices having a high probability of identifying a target material are dual energy CT scanned.

Locations at or near each identified object 28 are single energy CT scanned 306 based on a single energy algorithm. CT scan 306 includes a low energy scan or a high energy scan of each identified location within container 12. A single energy slice plan is generated 308 using the scan information obtained during CT scan 306. In one embodiment, the high energy scan information including CT number information is utilized to facilitate determining whether object 28 includes a target material, such as an explosive material.

A decision is made 310 based on the acquired scan information as to whether container 12 includes one or more objects 28 of interest. The decision is at least partially made based on whether scanning system 10 determines that an object within container 12 has a CT number similar to a CT number for a target material, such as an explosive material. If no object 28 of interest is identified based on the scan information obtained during single energy CT scan 306, a determination is made 312 as to whether additional slices are required to clear container 12. If no additional slices are required to clear container 12, container 12 is ejected 314 from within scanning system 10. However, if additional slices are required 316 to clear container 12, an additional single energy CT scan 306 is performed. Such process is repeated until no additional slice is required, and scanning system 10 makes a determination based on available information to clear and eject 314 container 12 from within scanning system 10.

Upon identifying one or more objects 28 of interest, each object 28 is dual energy CT scanned 320 based on a single energy algorithm or a dual energy algorithm. Dual energy CT scan 320 includes one or more low energy scans and one or more high energy scans of each identified object 28 of interest within container 12 for slices associated with object 28. In this embodiment, the low energy scan information and/or the high energy scan information may be utilized to facilitate determining whether each object 28 of interest includes a target material. Using a suitable algorithm, scanned data corresponding to additional cross-sectional slices of each object 28 are obtained and transmitted to data collection system 18. Data collection system 18 and/or processor 20 calculates the CT number distribution and/or the atomic number distribution within the cross-sectional slices of object 28 and processes the data collected to facilitate determining whether object 28 includes a target material. Processor 20 then determines 312 whether one or more additional slices are required. If an additional slice is required 316, dual energy CT scan 320 is performed to generate additional high energy information and additional low energy information utilized to facilitate determining whether object 28 includes a target material.

Based on the scan information obtained during dual energy CT scan 320, a determination is made 312 as to whether additional slices are required to clear container 12. If no additional slices are required to clear container 12, container 12 is ejected 314 from within scanning system 10. However, if additional slices are required 316 to clear container 12, an additional single energy CT scan 306 is performed. Such process is repeated until no additional slice is required, and scanning system 10 makes a determination based on available information to clear and eject 314 container 12 from within scanning system 10.

Figure 5:
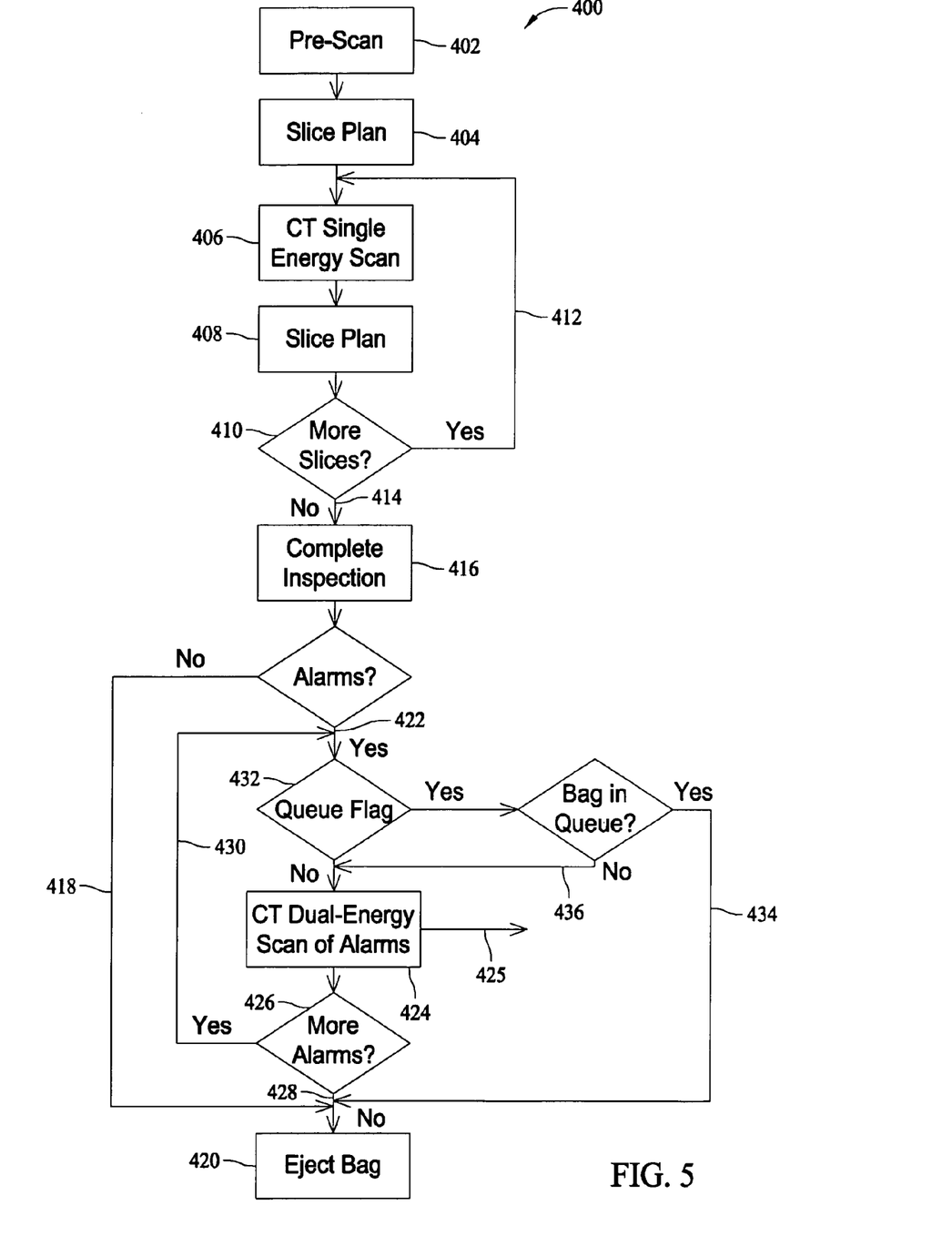
FIG. 5 shows a flow chart for an alternative exemplary method for inspecting containers for target materials using the system shown in FIG. 1.

FIG. 5 shows a flow chart illustrating an exemplary method 400 for inspecting container 12, such as checked luggage, to identify one or more objects concealed within container and performing a targeted scan of each identified object to verify whether the object is a safety threat, e.g., a target material, such as an explosive material.

Referring further to FIG. 5, a prescan stage 402 is employed to perform a scan of container 12. In one embodiment, a suitable X-ray radiographic scan of container 12 is performed during prescan stage 402 to identify locations within container 12 that may require additional inspection. As described in greater detail below, based at least partially on projection data generated during prescan stage 402, a first or initial slice plan is generated 404. Using a suitable algorithm, scanned data corresponding to additional cross-sectional slices of container 12 are obtained and transmitted to data collection system 18 (shown in FIG. 1). In one embodiment, data collection system 18 and/or processor 20 (shown in FIG. 1) processes the data collected to facilitate identifying one or more locations of interest within container 12. In this embodiment, only the identified locations are CT scanned to facilitate maintaining system throughput.

In this embodiment, one or more identified locations within container 12 are single energy CT scanned 406 based on a single energy algorithm. Single energy CT scan 406 includes a low energy scan or a high energy scan of one or more identified locations within container 12. A single energy slice plan is generated 408 using the scan information, such as the high energy scan information obtained by the high energy scan, or, alternatively, the low energy scan information obtained by the low energy scan, obtained during single energy CT scan 406. In one embodiment, the high energy scan information includes CT number information that may be utilized to facilitate determining whether object 28 includes a target material, such as an explosive material.

Using a suitable algorithm, scanned data corresponding to additional cross-sectional slices of container 12 are obtained and transmitted to data collection system 18. Data collection system 18 and/or processor 20 calculates the CT number distribution within the cross-sectional slices of container 12 and processes the data collected to facilitate identifying one or more locations of interest within container 12. Processor 20 then determines 410 whether one or more additional slices are required to obtain additional scan information. If an additional slice is required 412, single energy CT scan 406 is performed to generate additional high energy information utilized to facilitate identifying locations that may include objects 28 of interest within container 12.

When no additional slice is required 414, scanning system 10 employs an algorithm to determine 416, based on available information, whether to generate an alarm signal or to clear container 12. If container 12 is cleared 418, container 12 is ejected 420 from within scanning system 10. However, if an alarm signal is generated 422, a post detection dual energy CT scan 424 of container 12 is performed. Post detection dual energy CT scan 424 scans only identified locations within container 12 suspected of including object 28 of interest. Post detection dual energy CT scan 424 includes high energy scan information corresponding to the CT number of object 28. A combination of the low energy scan information and the high energy scan information corresponds to the atomic number of object 28. The scan information obtained during post detection dual energy CT scan 424 is utilized to determine whether to clear and eject 420 container 12 from within scanning system 10. More specifically, during post detection classification both the high energy scan information related to the CT number of object 28 and the combination of the low energy scan information and the high energy scan information related to the atomic number of object 28 are collected and processed to determine 426 whether object 28 includes a target material, such as an explosive material.

If, based on the dual-energy scan information, it is determined that object 28 includes an explosive material, container 12 is subject to further inspection. However, if, no additional alarm signal was generated 428, container 12 is ejected 420 from within scanning system 10. If one or more additional alarm signals were generated 430, container 12 is scanned at post detection dual energy CT scan 424. Such process continues until scanning system 10 determines that at least one object 28 concealed within container 12 includes an explosive material or all objects 28 that resulted in an alarm signal generation have been scanned by post detection dual energy CT scan 424. If scanning system 10 determines that at least one object 28 includes a target material, such as an explosive material, container 12 is removed 425 from within scanning system and subject to additional inspection. If, upon scanning each object 28 responsible for generating an alarm signal, no object 28 has been determined to include an explosive material, container 12 is ejected 420 from within scanning system 10.

Referring to FIG. 5, in an alternative embodiment, the algorithm includes a queuing query to determine 432 whether another container 12 is queued for inspection. If scanning of container 12 generates an alarm signal 422 and one or more containers 12 are queued 434 for scanning by scanning system 10, container 12 is ejected 420 from within scanning system 10 and subject to additional inspection, such as by a TSA agent operating scanning system 10. However, if no other container 12 is queued 436, post detection dual energy CT scan 424 of container 12 is performed and the process continues as described above. In this embodiment, system throughput is maintained or increased by skipping the clearing stage including the dual energy CT scan of object(s) 28 responsible for generating an alarm signal if additional containers 12 are queued for scanning. Containers 12 that generate an alarm signal are removed from within scanning system 10 and physically inspected by a TSA agent, allowing scanning system 10 to continue to scan additional containers 12 queued for inspection.

In one embodiment, a computed tomography (CT) scanning system for automatically inspecting a container for a target material is configured to perform an initial radiographic scan of the container. Based at least partially on projection data generated during the initial radiographic scan, a slice plan with at least one location within the container that may require a single energy CT inspection is identified. The slice plan is adjusted as additional single energy scans are performed. Once the slice plan requires no more single energy scans, an automatic detection algorithm is used to identify objects of interest. If one or more objects of interest are identified, a slice plan of the at least one object of interest is generated and a dual energy CT scan of the at least one identified object of interest is performed. The dual energy CT scan includes a low energy scan of the at least one identified object of interest and a high energy scan of the at least one identified object of interest. Based at least partially on dual energy scan information generated during the dual energy CT scan, a determination is made whether the object contains a target material. If one or more objects contain the target material an alarm signal is generated for the container.

In an alternative embodiment, X-ray detector 16 is an energy sensitive detector, such a CZT or a dual-layer detector. In this embodiment, the scan data is collected at the high energy distribution and X-ray detector 16 provides the dual energy scan information to determine the effective atomic number of the inspected object. With a dual-layer detector, the layers are optimized to produce similar statistical accuracy for both the high energy distribution and the low energy distribution. In one embodiment, an operating mode for energy-sensitive X-ray detector 16 includes performing CT scans at locations identified by the prescan stage. Scanning system 10 produces an alarm/clear decision with all the available information. In an alternative embodiment, the operating mode includes CT scanning container 12 identified by the prescan stage employing a single energy algorithm, which produces an alarm/clear decision. If one or more objects generate an alarm signal, additional image analysis using dual energy scan information is performed to clear or confirm the alarm signal.

In summary, the above-described CT scanning system and method for inspecting containers, such as bulk break cargo and/or checked luggage or suitcases, for target materials including, without limitation, contraband, explosive materials, drugs, and/or weapons, include a radiographic prescan stage to identify areas or locations of interest within the container that are suspected of including a target material. A CT scanning performed at these identified locations facilitates identifying one or more objects contained within the container as target materials. Additional processing is performed on each identified object to confirm or clear the target material. In an alternative embodiment, the system includes a radiographic scanner to identify areas of interest, a first high-energy CT scanning process to facilitate identifying one or more objects contained within the container, and a second low-energy or dual-energy CT scanning process for determining whether each object includes a target material. In one embodiment, dual energy scanning is achieved by collecting data for the same slice at a low energy distribution and then a high energy distribution without moving the object. In one embodiment, the data is collected using a 180° fan angle at both energy distributions. Alternatively, data is collected at at least one full rotation for the low energy distribution and at least a 180° fan angle for the high energy distribution, allowing employment of the same projection angles for both energy distributions to facilitate reconstructing the images.

In order to reduce photon starvation at the low energy distribution, in one embodiment, a current for the low energy scanning is increased to maintain the same or similar power as the high energy scanning. Alternatively or in addition, a number of revolutions for the low energy scanning is increased. For example, if a high energy voltage is 2V and a high energy current is I, switching to a low energy voltage, such as V, increases a low energy current to 2I, which results in an increase by a factor of 2 the number of low energy X-rays. If the number of rotations is increased from 0.5 to 2, the number of low energy X-rays increases by a factor of 4. Both changes result in an 8-fold increase in low energy X-rays.

The above-described system and method facilitate inspecting containers efficiently and reliably. More specifically, utilization of dual-energy scanning produces an additional signature, namely atomic number, which facilitates increasing system performance including increasing detection of objects of interest and/or reducing false alarms. In contrast to the above-described system and method, conventional inspection systems produce images of the CT number, which is approximately proportional to the density, of the scanned object contents. The detection algorithms utilized in the conventional inspection systems are primarily based on the detection of CT number characteristics of the object of interest. Often times, benign materials have similar CT numbers and masses as objects of interest. Thus, as benign materials are inspected, false alarms may be generated. The utilization of dual energy scan information provides atomic number information to facilitate identifying objects of interest and distinguishing these objects of interest from benign materials to reduce the false alarm rate. Implementation of at least a portion of the above-described system does not require sophisticated power supplies and/or detectors. Further, unlike other dual energy approaches, the low voltages and the high voltages are not an average voltage resulting from slow switching times. The above-described system also facilitates reducing photon starvation for the low energy inspection, which would otherwise reduce the system capability for reducing the false alarm rate.

Exemplary embodiments of a system and a method for inspecting containers are described above in detail. The system and the method are not limited to the specific embodiments described herein, but rather, components of the system and/or the steps of the method may be utilized independently and separately from other components and/or steps described herein. Further, the described system components and/or method steps can also be defined in, or used in combination with, other systems and/or methods, and are not limited to practice with only the system and method as described herein.

While the above-described system and method have been described in terms of various specific embodiments, those skilled in the art will recognize that the invention can be practiced with modification within the spirit and scope of the claims.

What is claimed is:

1. A method for automatically inspecting a container for a target material using a computed tomography (CT) scanning system, said method comprising:
    performing an initial radiographic scan of the container;
    identifying, based at least partially on projection data generated during the initial radiographic scan, a first slice plan with at least one location within the container that requires CT inspection;
    performing additional single energy scans to acquire additional projection data;
    adjusting the first slice plan using the additional projection data;
    identifying at least one object of interest using an automatic detection algorithm once the first slice plan requires no more single energy scans;
    if the at least one object of interest is identified, generating a second slice plan of the at least one object of interest;
    performing a dual energy CT scan of the at least one object of interest, the dual energy CT scan including a low energy scan of the at least one object of interest and a high energy scan of the at least one object of interest;
    determining, based at least partially on dual energy scan information generated during the dual energy CT scan, whether the at least one object of interest includes a target material; and
    generating an alarm signal for the container if the at least one object of interest includes the target material.

2. A method in accordance with claim 1, wherein performing a dual energy CT scan comprises calculating a CT number distribution within cross-sectional slices of the container and processing the dual energy scan information to determine an atomic number distribution to facilitate identifying the at least one object of interest within the container.

3. A method in accordance with claim 2, further comprising CT scanning only the at least one object of interest to facilitate maintaining system throughput.

4. A method in accordance with claim 1, wherein said performing a dual energy CT scan is based on the single energy algorithm, said method further comprising generating a single energy slice plan using first high energy scan information obtained during the dual energy CT scan, the first high energy scan information utilized to facilitate determining whether the at least one identified location includes the at least one object of interest.

5. A method in accordance with claim 4, further comprising performing a second dual energy CT scan of the at least one identified location to generate second high energy scan information utilized to facilitate identifying the at least one object of interest.

6. A method in accordance with claim 5, wherein said method further comprises determining based on the dual energy scan information whether to generate the alarm signal or to clear the container.

7. A method in accordance with claim 6, further comprising:
    generating the alarm signal;
    performing a post detection dual energy CT scan of the at least one object of interest; and
    determining whether to clear an alarm based on information obtained during the post detection dual energy CT scan.

8. A method in accordance with claim 7, wherein during the post detection dual energy CT scan, high energy scan information related to a CT number of the at least one object of interest and a combination of the high energy scan information and low energy scan information related to an atomic number of the at least one object of interest are processed to determine whether the at least one object of interest includes the target material.

9. A method in accordance with claim 1, further comprising:
    determining that the at least one identified location includes the at least one object of interest; and
    performing a CT scan to facilitate determining whether the at least one object of interest includes the target material.

10. A method in accordance with claim 9, further comprising:
    generating high energy scan information and low energy scan information corresponding to additional cross-sectional slices of the identified location; and
    transmitting to a data collection system the high energy scan information and the low energy scan information, the data collection system configured to calculate a CT number distribution and an atomic number distribution within the additional cross-sectional slices of the identified location to facilitate identifying the target material within the identified location.

11. A method in accordance with claim 1, further comprising:
    generating the first slice plan to scan the identified locations for objects having a CT number similar to a CT number of the target material; and
    performing a single energy CT scan of the container based on a single energy algorithm.

12. A method in accordance with claim 11, further comprising transmitting high energy scan information obtained during the single energy CT scan to a data collection system, the data collection system configured to calculate a CT number distribution within cross-sectional slices of the container to facilitate identifying the at least one object of interest within the container.

13. A method in accordance with claim 12, wherein the dual energy CT scan is performed only on the at least one object of interest.

14. A method in accordance with claim 11, further comprising generating a single energy slice plan using high energy scan information obtained during the single energy CT scan, the high energy scan information including CT number information utilized to facilitate determining whether the identified location includes the at least one object of interest.

15. A method in accordance with claim 14, further comprising bypassing the dual energy CT scan if no object of interest is identified based on the high energy scan information obtained during the single energy CT scan.

16. A method in accordance with claim 14, wherein, upon identifying the at least one object of interest, the dual energy CT scan is performed to facilitate determining whether the at least one object of interest includes the target material.

17. A method in accordance with claim 1, further comprising generating the alarm signal before performing the dual energy CT scan, wherein the dual energy CT scan only scans identified locations within the container suspected of including at least one object of interest.

18. A method in accordance with claim 17, wherein performing a dual energy CT scan of the at least one identified location further comprises obtaining high energy scan information corresponding to a CT number of the at least one object of interest and a combination of the high energy scan information and low energy scan information corresponding to an atomic number of the object of interest to facilitate determining whether the at least one object of interest includes the target material.

19. A method in accordance with claim 18, further comprising removing the container from the CT scanning system for further inspection if, based on the high energy scan information and the low energy scan information, the at least one object of interest includes the target material.

20. A method in accordance with claim 18, further comprising determining whether an additional alarm signal was generated for the container during the dual energy CT scan.

21. A method in accordance with claim 20, further comprising ejecting the container from within the CT scanning system if no additional alarm signal is generated.

22. A method in accordance with claim 20, further comprising performing a second dual energy CT scan if the additional alarm signal was generated for the container during the dual energy CT scan.

23. A method in accordance with claim 22, further comprising ejecting the container from within the CT scanning system if, upon scanning at least one object of interest responsible for generating the alarm signal, no object of interest includes the target material.

24. A method in accordance with claim 17, further comprising performing a query to determine whether a second container is queued for scanning.

25. A method in accordance with claim 24, wherein, if scanning of the container generates the alarm signal and the second container is queued for scanning by the CT scanning system, the container is ejected from within the CT scanning system for further inspection.

26. A method in accordance with claim 24, wherein, if scanning of the container generates the alarm signal and the second container is not queued for scanning, the dual energy CT scan of alarming objects within the container is performed.

27. A computed tomography (CT) scanning system for automatically inspecting a container for a target material, said CT scanning system comprising:
   an X-ray source;
   an X-ray detector; and
   a processor, said processor configured to:
   perform an initial radiographic scan of the container;
   identify, based at least partially on projection data generated during the initial radiographic scan, a first slice plan with at least one location within the container that requires a single energy CT inspection;
   adjust the first slice plan as additional single energy scans are performed;
   identify objects of interest using an automatic detection algorithm once the first slice plan requires no more single energy scans;
   if at least one object of interest is identified, generate a second slice plan of the at least one object of interest;
   perform a dual energy CT scan of the at least one identified object of interest, the dual energy CT scan comprising a low energy scan of the at least one identified object of interest and a high energy scan of the at least one identified object of interest;
   determine whether the at least one object of interest includes a target material based at least partially on dual energy scan information generated during the dual energy CT scan; and
   generate an alarm signal for the container if the at least one object of interest includes the target material.

28. A method for automatically inspecting containers for a target material using a computed tomography (CT) scanning system, said method comprising:
   identifying at least one location within a first container that requires CT inspection based at least partially on projection data generated during an initial radiographic scan;
   performing a dual energy CT scan of the at least one identified location within the first container, the dual energy CT scan including a low energy scan of the at least one identified location and a high energy scan of the at least one identified location;
   determining whether the at least one identified location includes an object of interest based on data acquired by the dual energy CT scan;
   when the at least one identified location includes the object of interest, generating an alarm;
   determining whether a second container is queued for scanning;
   when the second container is queued for scanning, ejecting the first container from within the CT scanning system for further inspection to determine if the object of interest includes the target material; and
   when the second container is not queued for scanning, performing a dual energy CT scan of the object of interest within the first container to determine if the object of interest includes the target material.

* * * * *